(12) United States Patent
Misener et al.

(10) Patent No.: US 11,937,972 B2
(45) Date of Patent: Mar. 26, 2024

(54) MEDICAL DEVICES WITH A QUICK RELEASE DRIVE CONNECTOR

(71) Applicant: Bard Access Systems, Inc., Salt Lake City, UT (US)

(72) Inventors: Anthony K. Misener, Bountiful, UT (US); Steffan Sowards, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 38 days.

(21) Appl. No.: 17/520,558

(22) Filed: Nov. 5, 2021

(65) Prior Publication Data

US 2022/0142607 A1 May 12, 2022

Related U.S. Application Data

(60) Provisional application No. 63/110,795, filed on Nov. 6, 2020.

(51) Int. Cl.
| | | |
|---|---|---|
| *A61B 8/00* | (2006.01) | |
| *A61B 8/02* | (2006.01) | |
| *A61B 8/08* | (2006.01) | |
| *A61B 8/12* | (2006.01) | |
| *A61B 90/00* | (2016.01) | |

(52) U.S. Cl.
CPC .............. *A61B 8/0841* (2013.01); *A61B 8/02* (2013.01); *A61B 8/0891* (2013.01); *A61B 8/12* (2013.01); *A61B 8/4254* (2013.01); *A61B 90/39* (2016.02); *A61B 2090/3925* (2016.02); *A61B 2562/0223* (2013.01)

(58) Field of Classification Search
None
See application file for complete search history.

(56) References Cited

U.S. PATENT DOCUMENTS

| | | | | |
|---|---|---|---|---|
| 5,249,585 | A | * | 10/1993 | Turner .................... A61N 1/403 607/116 |
| 5,810,741 | A | * | 9/1998 | Essen-Moller .......... A61B 5/03 600/529 |
| 8,388,541 | B2 | | 3/2013 | Messerly et al. |
| 8,781,555 | B2 | | 7/2014 | Burnside et al. |
| | | | (Continued) | |

FOREIGN PATENT DOCUMENTS

| | | |
|---|---|---|
| EP | 2474268 A1 | 7/2012 |
| EP | 2637568 A2 | 9/2013 |

OTHER PUBLICATIONS

PCT/US202/058343 filed Nov. 5, 2021 International Search Report and Written Opinion dated Feb. 23, 2022.

*Primary Examiner* — Serkan Akar
*Assistant Examiner* — Amal Aly Farag
(74) *Attorney, Agent, or Firm* — Rutan & Tucker LLP

(57) ABSTRACT

Disclosed herein, in some embodiments, are medical device systems including an elongate medical device having a proximal end including one or more sensor connectors, a distal end including one or more sensors or emitters communicatively coupled to the one or more sensor connectors, and a drive connector including one or more sensor connector attachments configured to detachably couple to the one or more sensor connectors. The one or more sensor connector attachments can be configured to drive the one or more sensors or emitters of the elongate medical device.

30 Claims, 8 Drawing Sheets

(56) References Cited

U.S. PATENT DOCUMENTS

| | | |
|---|---|---|
| 8,849,382 B2 | 9/2014 | Cox et al. |
| 9,445,743 B2 | 9/2016 | Kassab |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,636,031 B2 | 5/2017 | Cox |
| 9,649,048 B2 | 5/2017 | Cox et al. |
| 9,901,714 B2 * | 2/2018 | Lemon .................. A61M 25/09 |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| 2007/0167682 A1 * | 7/2007 | Goldfarb ............ A61B 1/00154 |
| | | 600/114 |
| 2007/0270688 A1 | 11/2007 | Gelbart et al. |
| 2011/0105954 A1 | 5/2011 | Cohen et al. |
| 2014/0031674 A1 | 1/2014 | Newman et al. |
| 2014/0188133 A1 | 7/2014 | Misener |
| 2015/0080762 A1 | 3/2015 | Kassab et al. |
| 2015/0320977 A1 * | 11/2015 | Vitullo ............... A61M 25/0606 |
| | | 604/510 |
| 2016/0278852 A1 * | 9/2016 | Sliwa ............... A61B 18/1492 |
| 2017/0215762 A1 * | 8/2017 | Burnside ............. A61B 5/6848 |
| 2017/0231572 A1 | 8/2017 | Lowery |
| 2018/0116551 A1 | 5/2018 | Newman et al. |
| 2018/0242881 A1 * | 8/2018 | Aman .................... A61B 5/283 |
| 2020/0306141 A1 * | 10/2020 | Meadows ............ A61B 5/6871 |
| 2020/0397505 A1 * | 12/2020 | Viswanathan ..... A61B 18/1492 |

\* cited by examiner

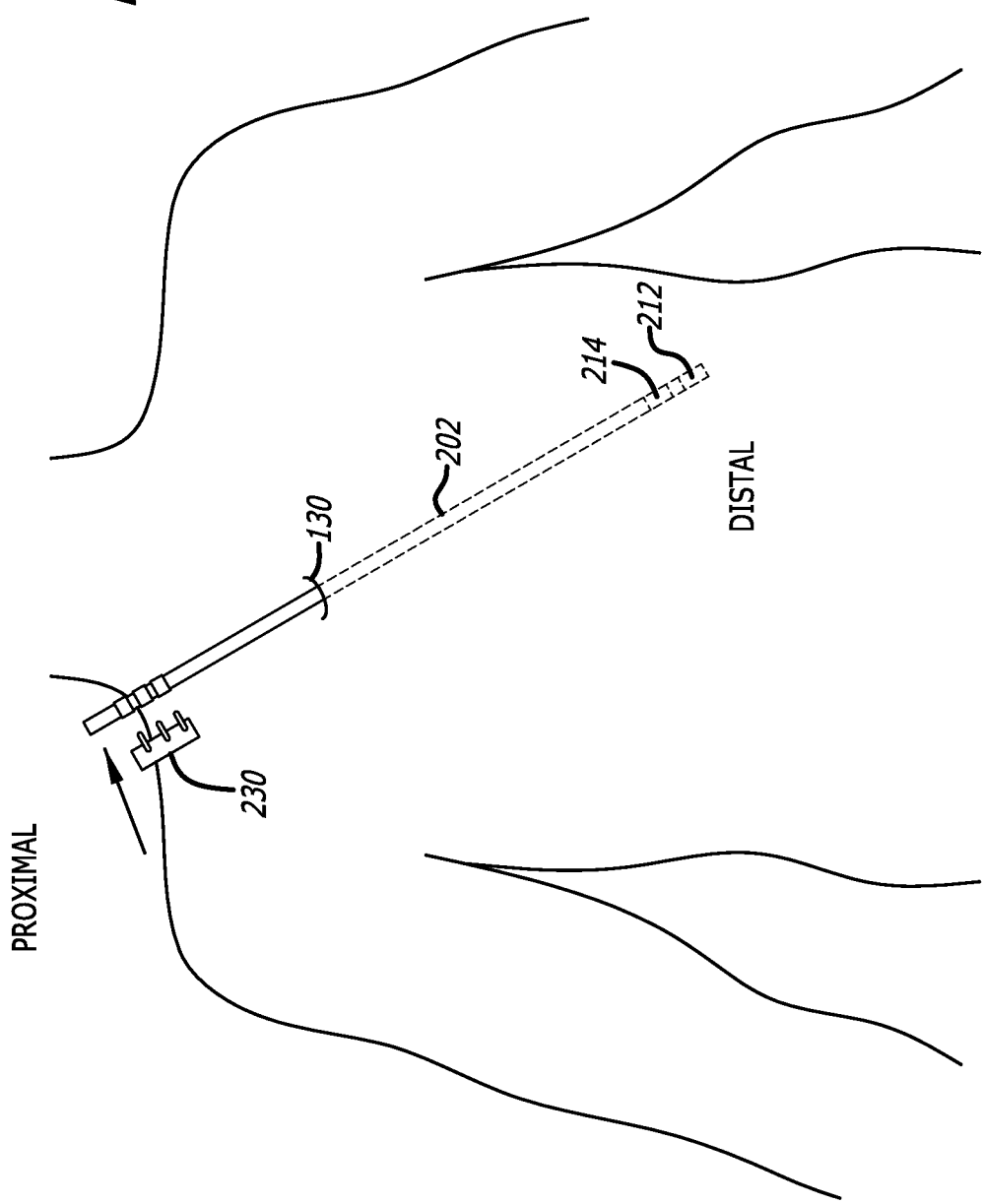

US 11,937,972 B2

MEDICAL DEVICES WITH A QUICK RELEASE DRIVE CONNECTOR

PRIORITY

This application claims the benefit of priority to U.S. Provisional Application No. 63/110,795, filed Nov. 6, 2020, which is incorporated by reference in its entirety into this application.

BACKGROUND

Many medical device implantation procedures require the upper chest to be unobstructed, to confirm, by imaging the target location, that the medical device has been placed in the proper anatomical location. Some of the medical device implantation procedures use guidewire or the like to place the medical device. It would be beneficial and time effective for the clinician to be able to configure the guidewire, stylet or similar to provide information about the guidewire's anatomical location during placement. However, configuring the guidewire, stylet, etc. could present issues preventing sliding of the medical device over the guidewire, stylet, etc. to a proper anatomical location. Disclosed herein are systems, apparatuses and a method that address the foregoing.

SUMMARY

Disclosed herein are systems and apparatuses that provide functionality to the elongate medical device used for introduction, such as a guidewire, stylet, introducer, etc., and/or to a catheter or other elongate medical device inserted into a patient. In some embodiments, the elongate medical device includes one or more sensors operably coupled to one or more sensor connectors. In some embodiments, the number of sensors is equivalent to the number of sensor connectors. A separate drive connector including one or more sensor connector attachments is designed for attachment to the elongate medical device at the one or more sensor connectors. In some embodiments, the number of sensor connector attachments is equivalent to the number of sensor connectors. The drive connector can be communicatively coupled to a console.

Although examples provided herein are with respect to a guidewire, other elongate medical devices are also contemplated, such as, for example, stylets, introducers, catheters or the like. In other words, the quick release drive connector should not be limited to use with guidewires only, but with any elongate device that would benefit from the concepts and examples described herein.

Disclosed herein is a medical device system including an elongate medical device having a proximal end and a distal end, the proximal end having one or more sensor connectors, the distal end having one or more sensors or emitters wired to the one or more sensor connectors and a drive connector having a housing body including one or more sensor connector attachments configured to detachably couple to the one or more sensor connectors to drive the one or more sensors or emitters of the elongate medical device.

In some embodiments, the medical device system includes the one or more sensor connector attachments extending from the housing body.

In some embodiments, the medical device system includes the housing body having a housing body cavity including the one or more sensor attachments located within the housing body cavity.

In some embodiments, the medical device system includes the drive connector communicatively coupled to a console.

In some embodiments, the medical device system includes the one or more sensors or emitters including one or more electromagnetic coils, one or more electrocardiogram sensors, or one or more impedance measuring devices.

In some embodiments, the medical device system includes the one or more sensor connectors including one or more electromagnetic coil connectors, one or more electrocardiogram sensor connectors, or one or more impedance measuring device connectors.

In some embodiments, the medical device system includes the one or more sensor connector attachments including one or more electromagnetic coil attachments, one or more electrocardiogram sensor attachments, or one or more impedance measuring device attachments.

In some embodiments, coupling of the drive connector to the elongate medical device is configured to stabilize the elongate medical device and prevent embolization of the elongate medical device.

In some embodiments, the housing body includes a thru drape connection. In some embodiments, the housing body is configured to be sterile disposable. In some embodiments, the drive connector is wired to the console. In some embodiments, the drive connector is wirelessly coupled to the console.

In some embodiments, one or more impedance measuring devices may be configured to do one or more of mapping the cross sectional area of one or more blood vessels, confirming the delivery of the elongate medical device to an anatomical target location in a body, or confirming the delivery of a medical device to an anatomical target location.

In some embodiments, one or more electrocardiogram sensors are configured to do one or more of confirming arrival of elongate medical device at an anatomical target location, confirming a depth of the elongate medical device, or confirming a length of the elongate medical device.

In some embodiments, the elongate medical device is selected from the group consisting of a guidewire, a stylet, an introducer, and a catheter. In some embodiments, the elongate medical device includes segmented depth markings.

Also disclosed herein is a medical device insertion system including a medical device system including a guidewire having a proximal end and a distal end, the proximal end having one or more sensor connectors, the distal end having one or more sensors or emitters wired to the one or more sensor connectors, the guide wire having segmented depth markings. The medical device system further includes a drive connector having a housing body including one or more sensor connector attachments configured to detachably couple to the one or more sensor connectors to drive the one or more sensors or emitters of the guidewire. The medical device insertion system includes an ultrasound imaging system including the console configured to receive information from the one or more sensors or emitters of the medical device system, the console having one or more logic modules coupled to memory, and the console communicatively coupled to a display and an ultrasound probe, and a medical device configured for insertion over the guidewire.

In some embodiments, the one or more sensor connector attachments extend from the housing body.

In some embodiments, the housing body includes a housing body cavity having the one or more sensor connector attachments within the housing body cavity.

In some embodiments, the drive connector is communicatively coupled to the console. In some embodiments, the one or more sensors or emitters includes one or more electromagnetic coils, one or more electrocardiogram sensors, or one or more impedance measuring devices. In some embodiments, the one or more sensor connectors includes one or more electromagnetic coil connectors, one or more electrocardiogram sensor connectors, or one or more impedance measuring device connectors. In some embodiments, the one or more sensor attachments include one or more electromagnetic coil attachments, one or more electrocardiogram sensor attachments, or more or more impedance measuring device attachments.

In some embodiments, the housing body includes a thru drape connection. In some embodiments, the housing body is configured to be sterile disposable.

In some embodiments, the one or more logic modules may be configured to perform one or more of determining the anatomical location of the guidewire, determining the depth or length of the guidewire, determining the anatomical location of the medical device threaded over the guidewire, or mapping one or more blood vessels. In some embodiments, the one or more logic modules determine the anatomical location of the guidewire through tracking the one or more sensors or emitters. In some embodiments, the one or more logic modules determine the anatomical location of the medical device through tracking the one or more sensors of the guidewire as the medical device is threaded on the guidewire. In some embodiments, the one or more logic modules map the one or more blood vessels through tracking the one or more sensors or emitters.

In some embodiments, the medical device insertion system includes an ultrasound probe having one or more electromagnetic sensors configured to detect a magnetic field.

In some embodiments, the medical device configured for insertion over the guidewire is selected from the group consisting of a catheter, a peripherally inserted central catheter, a central venous catheter, and a midline catheter.

Also disclosed herein is a method for implanting a medical device including inserting an insertion needle into a target site, feeding a guidewire of a medical device system into the target site, the medical device system including a guidewire having a proximal end and a distal end, the proximal end having one or more sensor connectors, the distal end having one or more sensors or emitters wired to the one or more sensor connectors. The medical device system further includes a drive connector having a housing body including one or more sensor connector attachments configured to detachably couple to the one or more sensor connectors to drive the one or more sensors or emitters of the guidewire. The method further includes coupling the drive connector to the guidewire, confirming the guidewire is in the desired anatomical location, detaching the drive connector from the guidewire, and sliding a medical device over the guidewire.

In some embodiments, the method includes the sensor connector attachments extending from the housing body.

In some embodiments, the method includes the housing body having a housing body cavity including the sensor connector attachments within the housing body cavity.

In some embodiments, the method includes the one or more sensors or emitters including one or more impedance measuring devices, one or more electrocardiogram sensors, or one or more electromagnetic coils.

In some embodiments, the method includes the one or more sensor connectors including one or more impedance measuring device connectors, one or more electrocardiogram sensor connectors, or one or more electromagnetic coil connectors.

In some embodiments, the method includes the one or more sensor connector attachments including one or more impedance measuring device attachments, one or more electrocardiogram sensor attachments, or one or more electromagnetic coil attachments.

In some embodiments, coupling the drive connector to the guidewire includes slidably engaging the drive connector with the proximal end of the guidewire.

In some embodiments, detaching the drive connector to the guidewire includes slidably disengaging the drive connector with the proximal end of the guidewire.

In some embodiments confirming the guidewire is in the desired anatomical location includes confirming with the one or more sensors or emitters and an ultrasound imaging system including a console having one or more logic modules, the console being coupled to a display and an ultrasound probe having one or more electromagnetic sensors.

In some embodiments, sliding the medical device over the guidewire includes confirming the medical device is in the target site with the one or more sensors or emitters and an ultrasound imaging system including a console having one or more logic modules, the console being coupled to a display and an ultrasound probe having one or more electromagnetic sensors.

In some embodiments, the method includes the medical device selected from a group consisting of a catheter, a peripherally inserted central catheter, a central venous catheter, a midline catheter, and an introducer.

In some embodiments, the method includes the target site including one or more blood vessels.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 4A-4C illustrate an exemplary method of placing a guidewire, in accordance with some embodiments.

DESCRIPTION

Figure 1A:
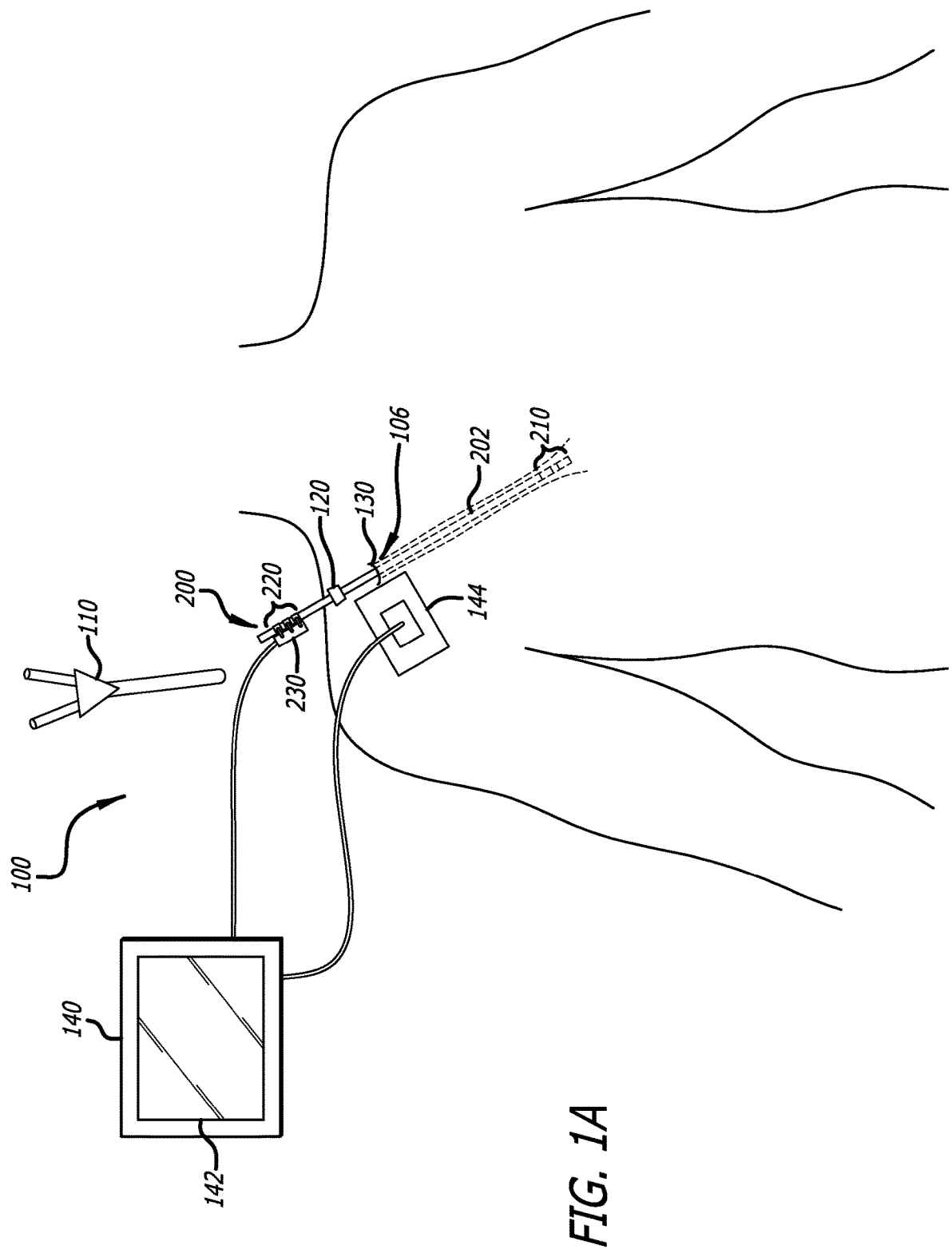
FIG. 1A illustrates a medical device insertion system including a medical device system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a guidewire disclosed herein includes a portion of the guidewire intended to be near a clinician when the guidewire is used on a patient. Likewise, a "proximal length" of, for example, the guidewire includes a length of the guidewire intended to be near the clinician when the guidewire is used on the patient. A "proximal end" of, for example, the guidewire includes an end of the guidewire intended to be near the clinician when the guidewire is used on the patient. The proximal portion, the proximal-end portion, or the proximal length of the guidewire can include the proximal end of the guidewire; however, the proximal portion, the proximal-end portion, or the proximal length of the guidewire need not include the proximal end of the guidewire. That is, unless context suggests otherwise, the proximal portion, the proximal-end portion, or the proximal length of the guidewire is not a terminal portion or terminal length of the guidewire.

With respect to "distal," a "distal portion" or a "distal-end portion" of, for example, a guidewire disclosed herein includes a portion of the guidewire intended to be near or in a patient when the guidewire is used on the patient. Likewise, a "distal length" of, for example, the guidewire includes a length of the guidewire intended to be near or in the patient when the guidewire is used on the patient. A "distal end" of, for example, the guidewire includes an end of the guidewire intended to be near or in the patient when the guidewire is used on the patient. The distal portion, the distal-end portion, or the distal length of the guidewire can include the distal end of the guidewire; however, the distal portion, the distal-end portion, or the distal length of the guidewire need not include the distal end of the guidewire. That is, unless context suggests otherwise, the distal portion, the distal-end portion, or the distal length of the guidewire is not a terminal portion or terminal length of the guidewire.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1A illustrates a medical device insertion system 100, in accordance with some embodiments. In some embodiments, the medical device insertion system 100 includes a medical device 110, a medical device system 200 including an elongate medical device 202 having one or more sensors or emitters 210 coupled to one or more sensor connectors 220, and a quick release drive connector ("drive connector") 230, detachably coupled to the one or more sensor connectors 220, configured to drive or provide electrical current to the one or more sensors or emitters 210. In some embodiments, the elongate medical device 202 includes a guidewire, a stylet, an introducer, a catheter or the like.

In some embodiments, the medical device insertion system 100 can further include an ultrasound probe 144 coupled to a console 140 having a one or more logic modules, the console 140 configured to use the information from the one or more sensors or emitters 210 and the ultrasound probe 144 to do one or more of the following: determine the anatomical location of the elongate medical device 202, determine the depth or length of the elongate medical device 202 after insertion, determine the anatomical location of the medical device 110 in a body or map one or more target blood vessels 106. In some embodiments, the medical device insertion system 100 further includes an insertion needle 120 configured to be inserted at a target site 130. In some embodiments, the target site 130 can include one or more target blood vessels 106. In some embodiments, the medical device 110 can include a catheter, peripherally inserted central catheter ("PICC"), central venous catheter ("CVC"), midline catheter, an introducer, a stylet or the like.

In some embodiment, the drive connector 230 may be configured to transmit the information detected by the one or more sensors or emitters 210 to the console 140. In an embodiment of using the medical device insertion system 100 to place the medical device 110, the insertion needle 120 can be inserted at the target site 130. In an embodiment, the elongate medical device 202 can include guidewire. The guidewire 202 may be configured to slide through the insertion needle 120 into the target site 130, and the drive connector 230 detachably coupled to the one or more sensor connectors 220. The drive connector 230 may be configured to drive the one or more sensors or emitters 210. The console 140 may be configured to obtain information from the one or more sensors or emitters 210 for placing the guidewire 202 in the target site 130. The ultrasound probe 144 may be configured to transmit ultrasound images of the guidewire 202 being placed in the target site 130, to the console 140. Once the guidewire 202 is placed at the proper anatomical location using the information gathered from one or more of: the one or more sensors or emitters 210 or the ultrasound images, the drive connector 230 can be detached from the one or more sensor connectors 220. The insertion needle 120 can be slidably removed, over the guidewire 202 from the target site 130. In some embodiments, the guidewire 202 can be used to facilitate placing the medical device 110. Advantageously, the medical device system 200 can be configured to selective drive the one or more sensors or emitters 210 for appropriately placing the guidewire 202, then remove the drive connector 230 from the guidewire 202 to easily thread additional medical devices over the guidewire 202. The drive connector 230 can then be re-coupled to the one or more sensor connectors 220 to obtain information from the one or more sensors or emitters 210 for medical device delivery confirmation or to stabilize the guidewire 202 to prevent embolization.

Figure 1B:
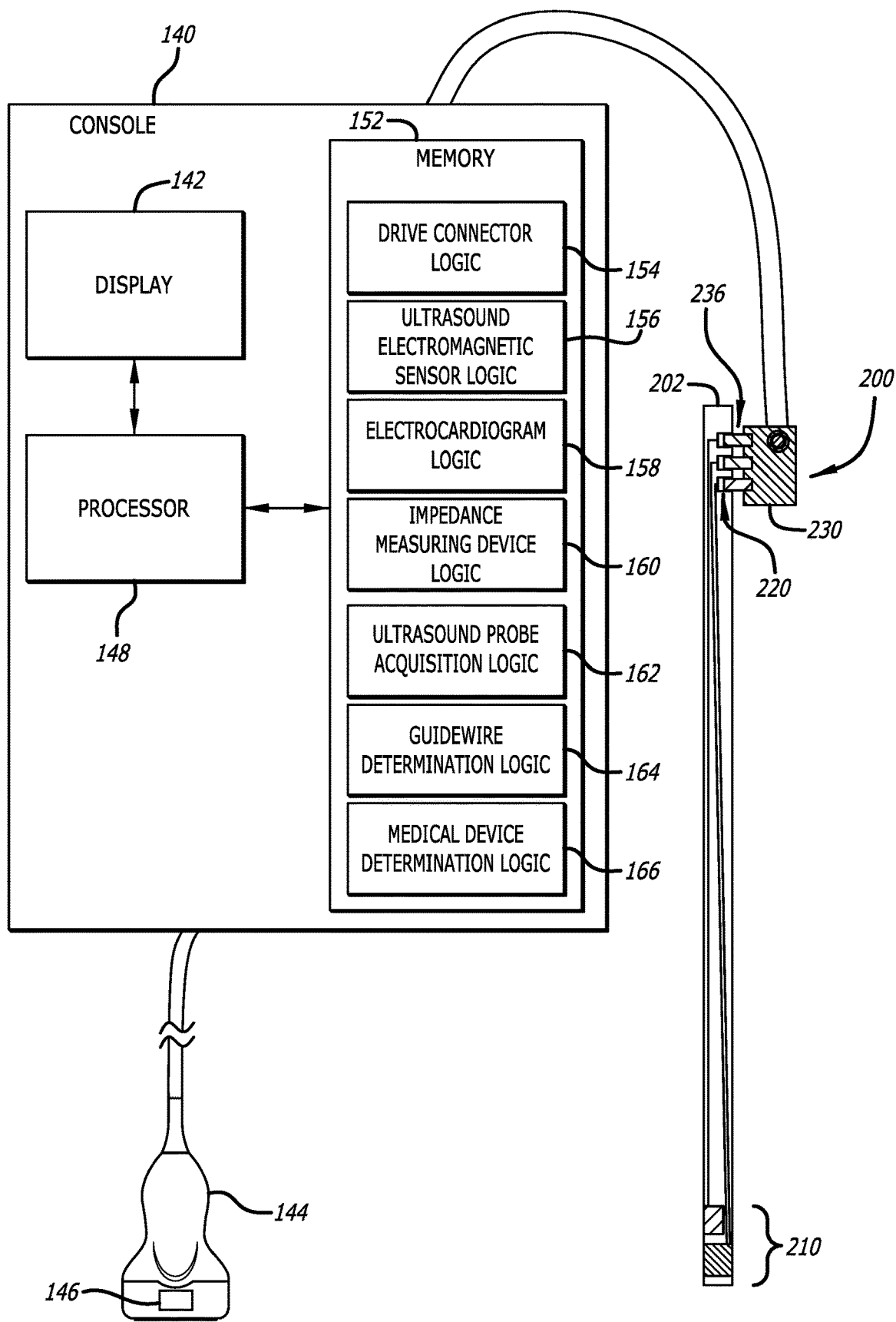
FIG. 1B illustrates a block diagram depicting various components of a medical device insertion system including a medical device system, in accordance with some embodiments.

FIG. 1B illustrates a block diagram depicting various components of a medical device insertion system 100 including the medical device system 200, in accordance with some embodiments. In some embodiments, the console 140 is communicatively coupled to the display 142. In some embodiments, the display 142 may be wired to the console 140 or wirelessly coupled to the console 140. Exemplary wireless communication modalities can include WiFi, Bluetooth, Near Field Communications (NFC), cellular Global System for Mobile Communication ("GSM"), electromagnetic (EM), radio frequency (RF), combinations thereof, of the like.

The console 140 may be coupled to the ultrasound probe 144. The ultrasound probe 144 may be configured to transmit ultrasound images to the console 140. In some embodiments as illustrated in FIG. 1B, the ultrasound probe 144 may include one or more electromagnetic sensors 146 for detecting a magnetic field. Details of exemplary multimodal tracking systems including ultrasound imaging systems can be found in U.S. Pat. Nos. 8,388,541, 8,781,555, 8,849,382, 9,445,743, 9,456,766, 9,492,097, 9,521,961, 9,554,716, 9,636,031, 9,649,048, 10,159,531, 10,172,538, 10,413,211, 10,449,330, U.S. Publication No. 2014/0031674, U.S. Publication No. 2014/0188133, U.S. Publication No. 2015/0080762, and U.S. Publication No. 2018/0116551, each of which are incorporated by reference in their entirety into this application.

In some embodiments, the console 140 may be communicatively coupled to the drive connector 230. In some embodiments, the drive connector 230 may transmit information from the one or more sensors or emitters 210 on the elongate medical device 202 to the console 140. In some embodiments, the console 140 may be configured to receive information from the one or more sensors or emitters, by way of an external sensor coupled to the console 140. In some embodiments, the console 140 includes a processor 148 and one or more logic modules coupled to non-transitory, computer-readable medium ("memory") 152. The one or more logic modules may be configured to include one or more of: a drive connector logic 154, an ultrasound electromagnetic sensor logic 156, an electrocardiogram logic 158, an impedance measuring device logic 160, an ultrasound probe acquisition logic 162, a guidewire determination logic 166 or a medical device determination logic 168. In some embodiments, the drive connector logic 154 may be configured to selectively drive one or more sensor connector attachments 236 and determine if adequate electrical current is being provided to the one or more sensors or emitters 210. In some embodiments, the ultrasound electromagnetic sensor logic 156 may be configured to acquire a detected magnetic field generated by an electromagnetic coil. In some embodiments, the electrocardiogram logic 158 may be configured to acquire an electrocardiogram signal generated by an electrocardiogram sensor on the guidewire 202. In some embodiments, the impedance measuring device logic 160 may be configured to acquire changes in an impedance signal from an impedance measuring device on the guidewire 202. In some embodiments, the ultrasound probe acquisition logic 162 may be configured to acquire ultrasound probe data. In some embodiments, the guidewire determination logic 164 may be configured to determine the anatomical location of the elongate medical device 202, determine the depth or length of the elongate medical device 202 or map the one or more blood vessels. In some embodiments, the medical device determination logic 166 may be configured to determine the anatomical location of the medical device 110 as the medical device 110 is configured to slide over the guidewire 202.

Figure 2A:
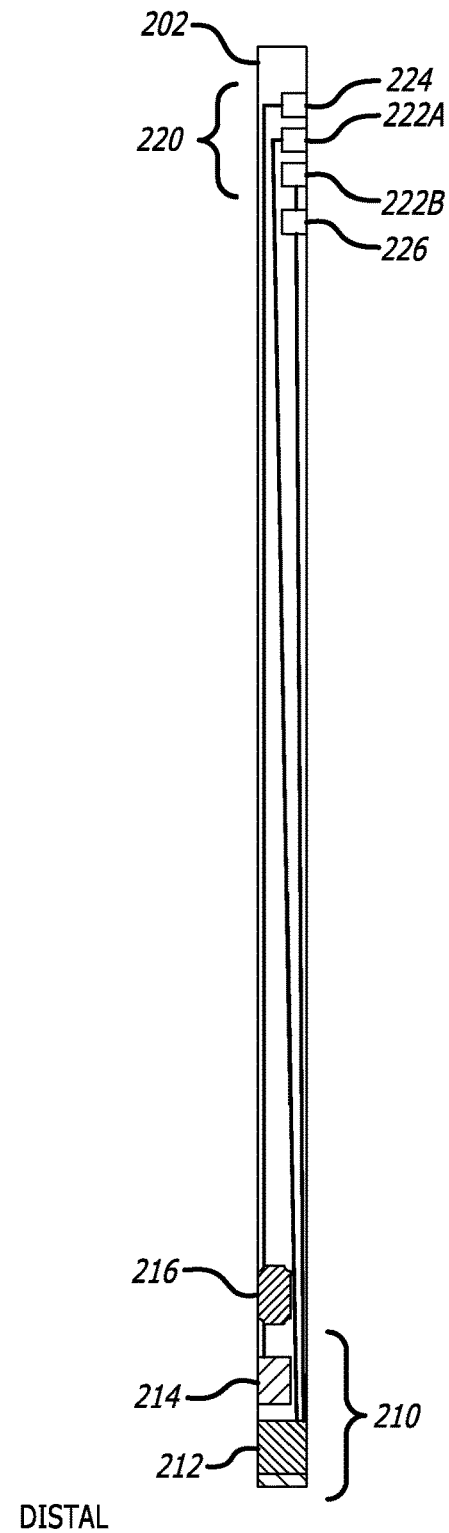
FIGS. 2A-2B illustrate a guidewire of a medical device system, in accordance with some embodiments.
Figure 2B:
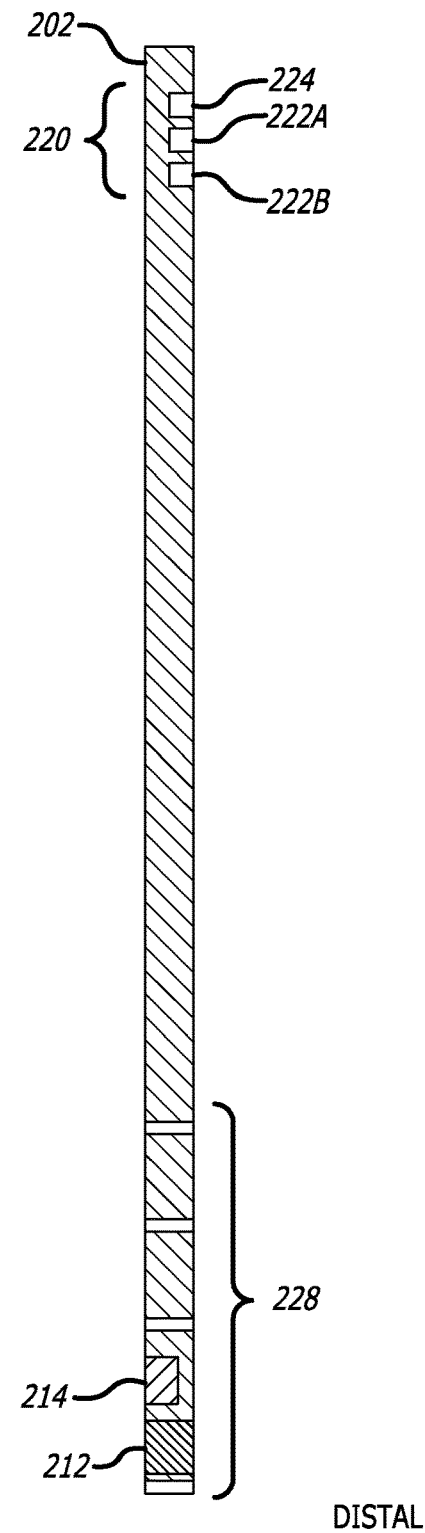

FIGS. 2A-2B illustrate a guidewire 202 of a medical device system 200, in accordance with some embodiments. As illustrated in FIG. 2A, in some embodiments, the one or more sensors or emitters 210 may be located at a distal end of the guidewire 202 and the one or more sensor connectors 220 may be located at the proximal end of the guidewire 202. In some embodiments, the one or more sensors or emitters 210 may include sensors or emitters configured to be sensed by an external sensor. In some embodiments, the one or more sensors or emitters 210 may be coupled, by wired connection, to the one or more sensor connectors 220. In some embodiments, the wired connection between the one or more sensors 210 and the one or more sensor connectors 220 may be contained within the guidewire 202. In some embodiments, number of sensors 210 is equivalent to the number of sensor connectors 220. In some embodiments, the one or more sensors 210 coupled to the one or more sensor connectors 220 include one or more of: an electrocardiogram (ECG) sensor 214 coupled to an ECG connector 224, an electromagnetic (EM) coil 212 coupled to a pair of EM connectors 222A/B, or an impedance measuring device 216 coupled to an impedance connector 226. In an embodiment, the EM coil 212 coupled to a pair of EM connectors 222A/B may include a plurality of EM coils coupled to a plurality of pairs of EM connectors. In this embodiment, the plurality of EM coils may be distributed evenly along the guidewire 202. In another embodiment, the plurality of EM coils may be distributed unevenly along the guidewire 202. In a preferred embodiment, the medical device system 200 may include a guidewire 202 having an EM coil 212 located at the distal end of the guidewire 202 wired to a pair of EM coil connectors 222A/B at the proximal end of the guidewire 202 configured to provide electrical current therebetween. In the preferred embodiment, the guidewire 202 further includes an ECG sensor 216 is located at the distal end of the guidewire 202 wired to an ECG sensor connector 226 at the proximal end of the guidewire 202.

In some embodiments, as illustrated in FIG. 2B, the guidewire 202 can include a plurality of depth indicators 228 on at least a portion the guidewire 202. In some embodiments, the plurality of depth indicators 228 may include indentations evenly space on the guidewire 202. In some embodiments, the plurality of depth indicators 228 may include radiopaque material evenly spaced on at least a portion of the guidewire 202. In some embodiments, the one or more sensors 210 and one or more sensor connectors 220 can be configured on the guidewire 202 to sit flush along the surface of the guidewire 202 to prevent any hindrance when the guidewire 202 is configured to slide into the target site 130 or when additional devices are configured to slide thereon.

Figure 3A:
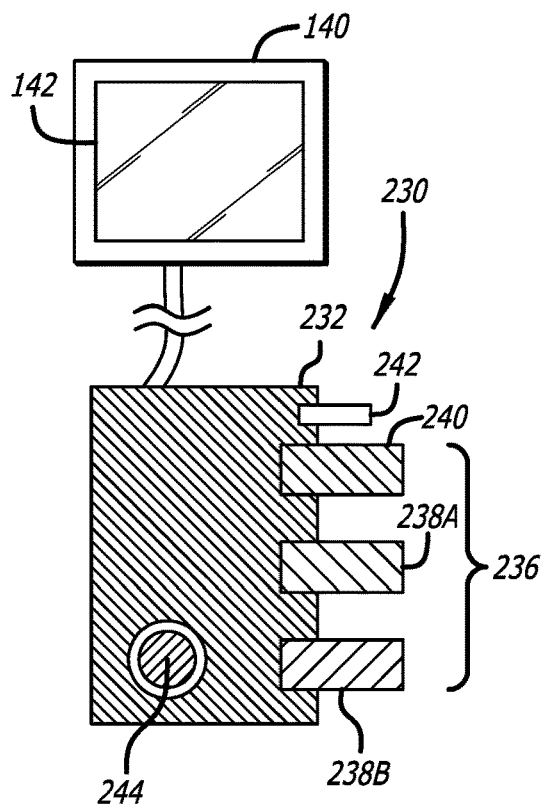
FIGS. 3A-3B illustrate a plan view of drive connectors, in accordance with some embodiments.
Figure 3B:
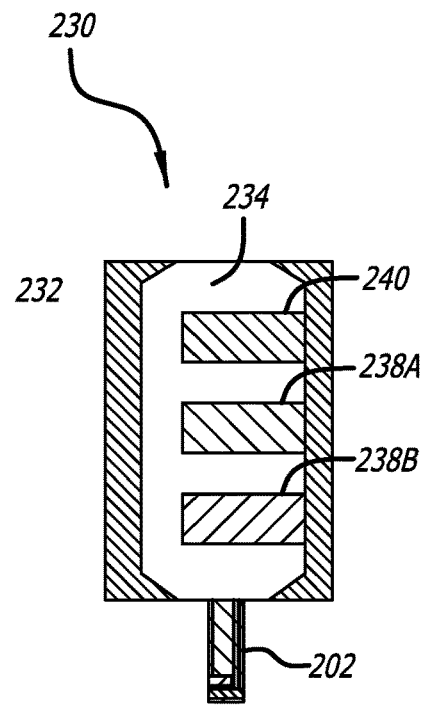

FIGS. 3A-3B illustrate a plan view of drive connectors 230, in accordance with some embodiments. The drive connector 230 may be configured to drive or provide electrical current to the one or more sensors or emitters 210 through coupling with the one or more sensor connectors 230. In some embodiments, the drive connector 230 is designed for attachment to an elongate medical device 202 at the one or more sensor connectors 220. The drive connector 230 includes a housing body 232 having one or more sensor connector attachments 236 configured to detachably couple to the one or more sensor connectors 220 on the guide wire 202. In some embodiments, the sensor connector attachments 236 may be configured to be quick-releasing as will be described in more detail herein.

In some embodiments, the one or more sensor connector attachments 236 may extend from the housing body 232. In an embodiment as illustrated in FIG. 3B, the housing body 232 may include a housing body cavity 234 having the one or more sensor connector attachments 236 therein. In this embodiment, a portion of the proximal end of the guidewire 202 may be configured to fit within the housing body cavity 234 with the one or more sensor connectors attachments 236 coupling with the one or more sensor connector 220 of the guidewire 202. In this embodiment, the housing body 232 may be configured to slidably engage the proximal end of the guidewire 202. In some embodiments, the housing body 232 may be configured to be sterile disposable, configured with a thru-drape connection configured to mate with the guidewire 202 below a sterile drape or a combination thereof. In some embodiments, sterile disposable includes the housing body 232 being pre-sterilized and single use disposable.

The drive connector 230 may be configured to provide information from the one or more sensors or emitters 210 to the console 140. In some embodiments, the drive connector 230 may be configured to be wired to the console 140 or in wireless communication with the console 140. Exemplary wireless communication modalities can include WiFi, Bluetooth, Near Field Communications (NFC), cellular Global System for Mobile Communication ("GSM"), electromagnetic (EM), radio frequency (RF), combinations thereof, of the like. In some embodiments, the drive connector 230 may be configured to provide information from one or more but not all of the sensors or emitters 210. For example, when the one or more sensors or emitters 210 include an EM coil 212 and an ECG sensor 216, the drive connector 230 may be configured to be drive the EM coil 212 to generate an electromagnetic field that is configured to be detected by an external sensor coupled to the console 140 (e.g., the electromagnetic sensor 146 on the ultrasound probe 144) while the drive connector 230 transmits information from the ECG sensor 216 to the console 140.

In some embodiments, when the drive connector 230 is wired to the console 140, the console 140 may be configured to provide the electrical current necessary to drive the one or more sensors or emitters 210. In some embodiments, when the drive connector 230 is in wireless communication with the console 140, the housing body 232 may be configured to include an energy source 270 configured to provide electrical current to the one or more sensors or emitters 210. In some embodiments, detaching the drive connector 230 from the guidewire 202 breaks the electrical current to the one or more sensors or emitters 210. In some embodiments, breaking the electrical current to the one or more sensors or emitters 210 can break the information emitted or transmitted from the one or more sensors or emitters 210 to the console 140 until the electrical current is reestablished by coupling the drive connector 230 to the guidewire 202.

In some embodiments, as illustrated in FIG. 3A, the drive connector 230 may have an indicator 244 (e.g., LED, tactile feedback, or auditory feedback) or provide an indicator (e.g., visual message on a display coupled to the console or auditory message originating from the console 140) when the one or more sensor connector attachments 236 are adequately or inadequately coupled to the one or more sensor connectors 220. For example, if the one or more sensor connector attachments 236 are inadequately coupled to the one or more sensor connectors 220, an LED could flash indicating an inadequate connection has been formed between the one or more sensor connector attachments 236 and the one or more sensor connectors 220. In some embodiments, the console 140 may be configured to provide indicators that the console 140 is receiving information from the one or more sensors or emitters 210, indicating a proper connection between the drive connector 230 and the guidewire 202 has been formed and the one or more sensors or emitters 210 has sufficient electrical current. In some embodiments the console 140 may be configured to provide indicators that the console 140 is not receiving information from the one or more sensors or emitters 210, indicating a proper connection between the drive connector 230 and the guidewire 202 has not been formed or the one or more sensors or emitters 210 does not have sufficient electrical current. In an embodiment, the drive connector 230 may be configured to include a configuration of all sensor connector attachments 236 (e.g., one or more ECG sensor connector attachments 240, one or more pairs of EM connector attachments 238A/B, or one or more impedance measuring device attachments 242) that may be used with a guidewire 202 having any number or configuration of the one or more sensors or emitters 210. In this embodiment, the user may configure the drive connector 230 or the console 140 to only provide electrical current to the desired one or more sensors or emitters 210.

Figure 3C:
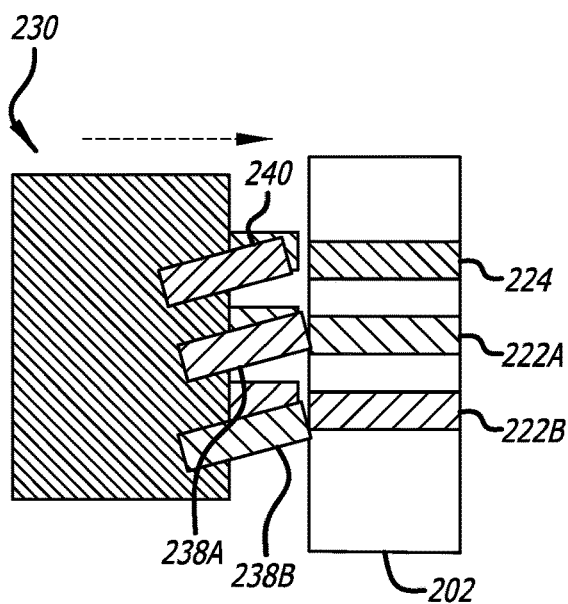
FIGS. 3C-3D illustrate an exemplary method of detachably coupling the drive connector of FIG. 3A. to the guidewire of a medical device system, in accordance with some embodiments.
Figure 3D:
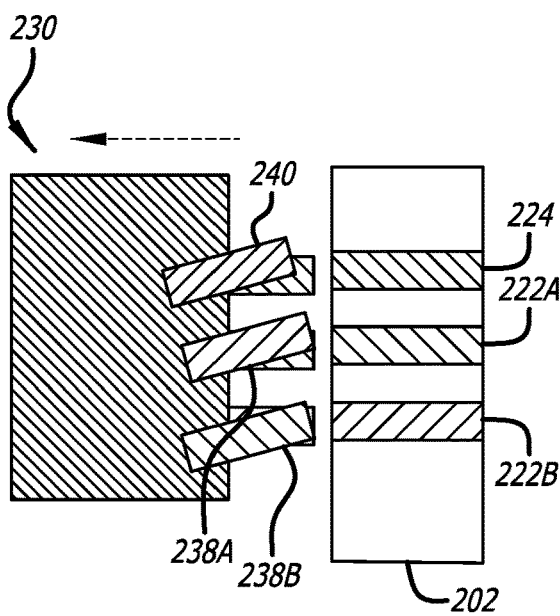

FIGS. 3C-3D illustrate an exemplary method of detachably coupling the drive connector 230 to the guidewire 202, in accordance with some embodiments. As illustrated in FIG. 3C, the drive connector 230, through the one or more sensor connector attachments 236, can detachably couple to the one or more sensor connectors 220. In some embodiments, the sensor connector attachments 236 may be configured to be quick-releasing. In some embodiments, the one or more sensor connector attachments 236 can be configured in a way to only detachably couple with the one or more sensor connectors 220 in a proper orientation. For example, the one or more EM coil connector attachment 238A/B may be configured in a way to only detachably couple with the one or more EM coil connector 222A/B. If the one or more EM coil connector attachment 238A/B attempts to detachably couple with an ECG sensor connector 224, the one or more EM coil connector attachment 238A/B may not be able to couple with the ECG sensor connector 224 or the drive connector 230 may not provide sufficient electrical current to power to the ECG sensor 214. In some embodiments, the drive connector 230 can only drive the one or more sensors or emitters 210 when the one or more sensor connector attachments 236 are properly coupled to the one or more sensor connectors 220. For example, the one or more EM coil connector attachments 238A/B can only provide sufficient electrical current to drive the EM coil 212 when the one or more EM connector attachments 238A/B is coupled to the pair of EM coil connector 222A/B. In some embodiments, the one or more sensor connector attachments 238 can detachably couple with the one or more sensor connectors 220 through a spring loaded clamping interaction, a magnetic interaction, a snap fit, a press fit, a quick release interaction, an interference fit or the like. The drive connector 230 can be brought to the guidewire 202 and the one or more sensor connector attachments 236 can be clamp fit onto the respective one or more sensor connectors 220. As illustrated in FIG. 3D, the one or more sensor connector attachments 236 can be quick released from the one or more sensor connectors 220 and the drive connector 230 can be pulled away from the guide wire 202.

Figure 3E:
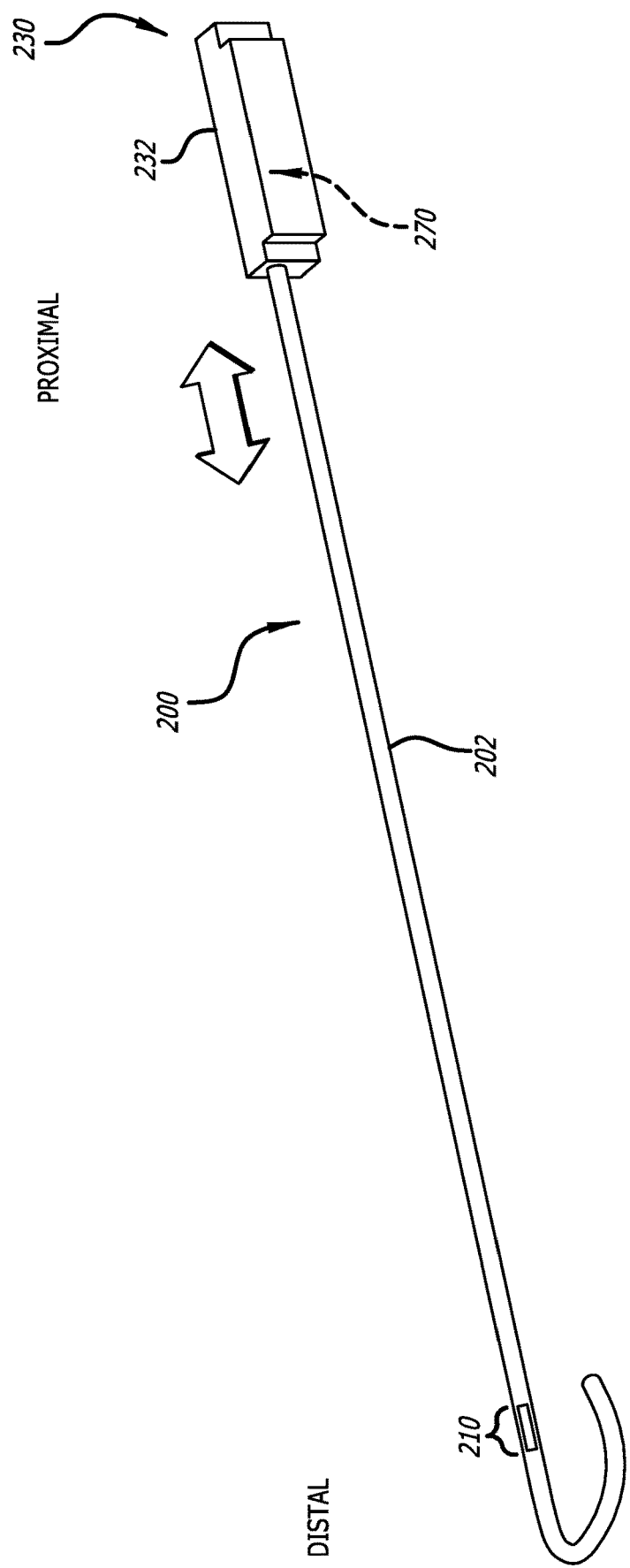
FIG. 3E illustrates an exemplary method for detachably coupling the drive connector of FIG. 3B to a guidewire of the medical device system, in accordance with some embodiments.

FIG. 3E illustrates an exemplary method for detachably coupling the drive connector 230 of FIG. 3B to a guidewire 202 of the medical device system 200, in accordance with some embodiments. The drive connector 230 may include one or more sensor connector attachments 236 within the housing body 232. The drive connector 230 may be configured to slide onto the proximal end of the guidewire 202, the one or more sensor connector attachments 236 engaging the one or more sensor connectors 220 of the guidewire 202. The or more sensor connector attachments 236 engaging the one or more sensor connectors 220 may configure the energy source 270 to drive the one or more sensors or emitters 210.

Figure 4B:
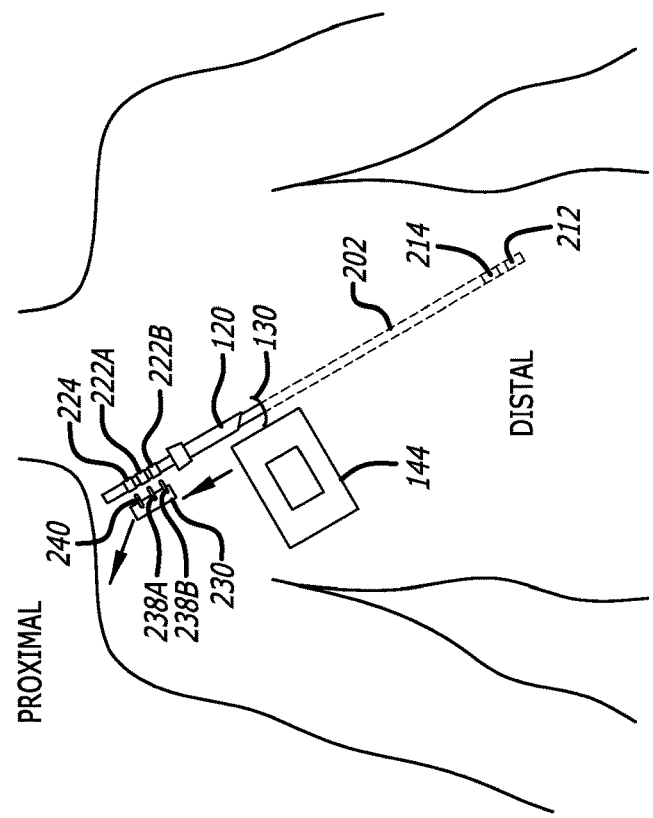
Figure 4A:
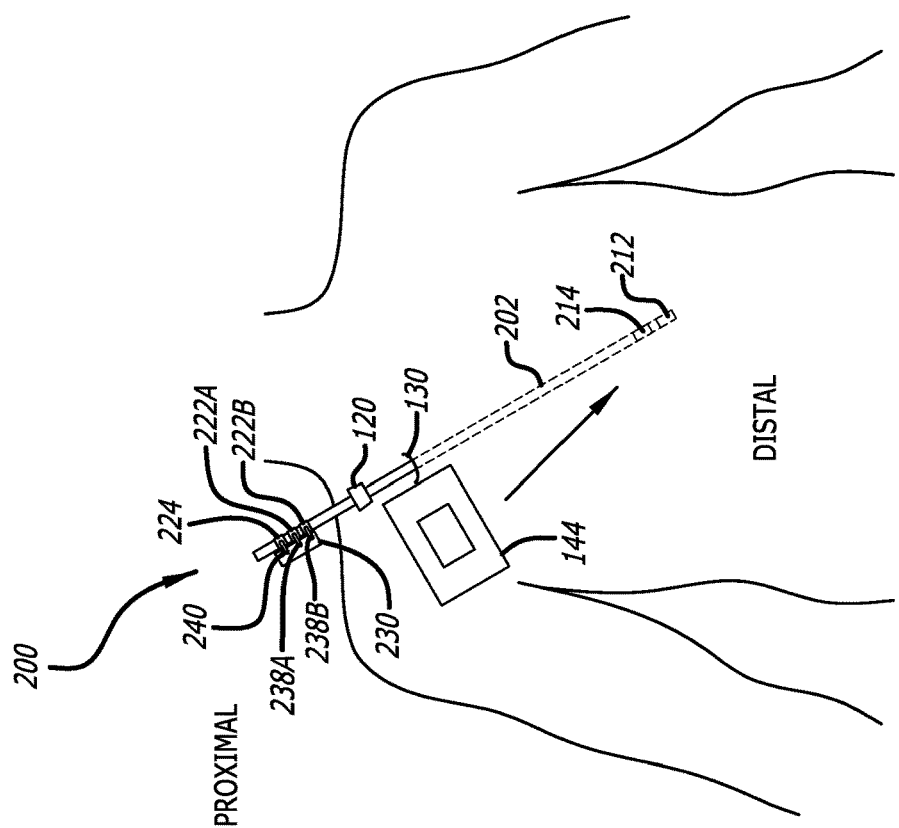

FIGS. 4A-4C illustrate an exemplary method of placing a guidewire 202 of the medical device system 200, in accordance with some embodiments. The medical device system 200 includes the guidewire 202 having the EM coil 212 at the distal end of the guidewire 202, coupled to the pair of EM coil connectors 222A/B at the proximal end of the guidewire 202 and the ECG sensor 214 at the distal end of the guidewire 202 coupled to the ECG connector 224 at the proximal end of the guidewire 202. The drive connector 230 includes the pair of EM coil connector attachments 22238A/B and the ECG connector attachment 240. In FIG. 4A, the guide wire 202 can be inserted into the target site 130 through the insertion needle 120. In some embodiments, the target site 130 includes one or more target blood vessels 106. The drive connector 230 can be detachably coupled to the guidewire 202 with the pair of EM coil connector attachments 238A/B coupling to the pair of EM coil connectors 222A/B and the ECG connector attachment 240 coupling to the ECG connector 224. The drive connector 230 may then be configured to drive the EM coil 212 through the pair of EM coil connectors 222A/B and receive information from the ECG sensor 214. Simultaneously, the ultrasound probe 144 may be configured to capture and transmit ultrasound images of the guidewire 202 moving to the proper anatomical location. In some embodiments, the ultrasound probe 144 may be configured to detect the magnetic field of the EM coil 212. The information from the ECG sensor 214, the images from the ultrasound probe 144 and the detection of the magnetic field generated by the EM coil 212 by the ultrasound probe 144 can be used to further guide the guidewire 202 to the proper anatomical location. Once the guidewire 202 is placed, as illustrated in FIG. 4B, the drive connector 230 can be removed and the insertion needle 120 can be removed from the target site 130 over the guidewire 202. A medical device 110 may be configured to threaded thereon. As illustrated in FIG. 4C, the drive connector 230 can be re-coupled to the guidewire 202 at any time to drive the EM coil 212 and ECG sensor 214. The information from the EM coil 212 and ECG sensor 214 can be used to provide delivery confirmation of the medical device 110 while being threaded on the guidewire 202. Furthermore, re-coupling the drive connector 230 to the guidewire 202 may prevent embolization of the guidewire 202.

Figure 5:
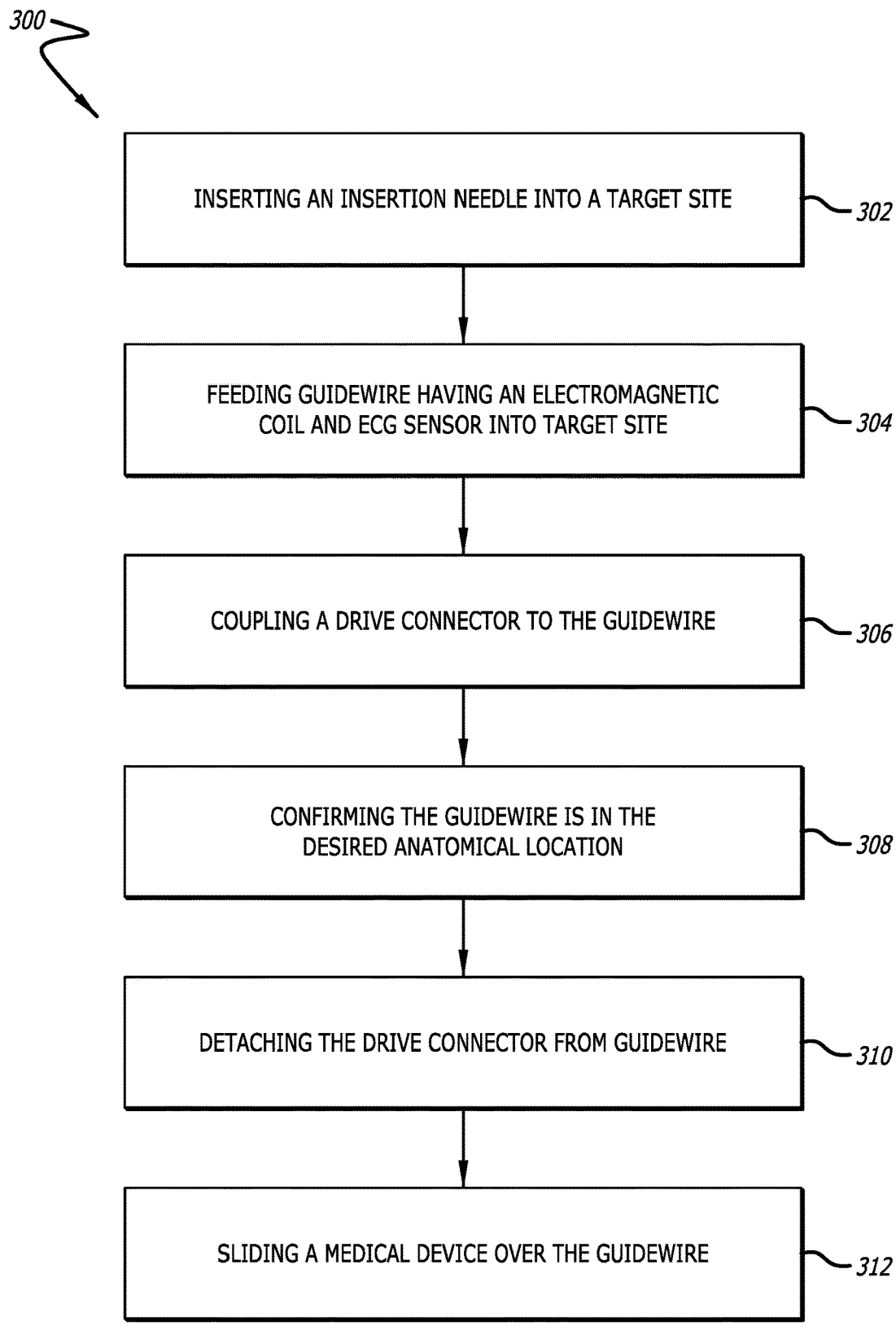
FIG. 5 illustrates a block diagram of an exemplary method for implanting a medical device, in accordance with some embodiments.

FIG. 5 illustrates a block diagram of a method 300 of implanting a medical device 110, in accordance with some embodiments. The method 300 includes inserting an introducer needle 120 into a target site 130 (block 302). In some embodiments, the target site 130 includes a target blood vessel 106. In some embodiments, the method 300 further includes feeding a guidewire 202 of a medical device system 200 into the target site 130 (block 304). In some embodiments, the medical device system 200 includes a guidewire 202 having a proximal end and a distal end, the proximal end having one or more sensor connectors 220 including a pair of EM coil connectors 222A/B and a ECG sensor connector 224, the distal end having one or more sensors or emitters 210 including an EM coil 212 and an ECG sensor 214 wired to the sensor connectors. The medical device system 200 further includes a drive connector having a housing body including one or more sensor connector attachments 236 including a pair of EM coil attachments 238A/B and an ECG sensor attachment 240 extending therefrom, the pair of EM coil attachments 238A/B and the ECG sensor attachment 240 configured to detachably couple to the pair of EM coil connectors 222A/B and the ECG sensor connector 224 to drive the EM coil 212 and the ECG sensor 214.

The method 300 further includes coupling the drive connector 230 to the guidewire 202 (block 306) to drive the EM coil 212 and the ECG sensor 214 and prevent embolization of the guidewire 202. In some embodiments, coupling the drive connector 230 to the guidewire 202 includes connecting the pair of EM coil attachments 238A/B to the pair of EM coil connectors 222A/B and the ECG sensor attachment 240 to the ECG sensor connector 224. In some embodiments, coupling the drive connector 230 to the guidewire 202 includes slidably engaging the drive connector 230 with the proximal end of the guidewire 202. In some embodiments, slidably engaging includes sliding the drive connector 230 distally on the proximal end of the guidewire 202. The method 300 further includes confirming the guidewire 202 is in the desired anatomical location (block 308). In some embodiments, confirming the guidewire 202 is at the desired anatomical location includes using one or more of the EM coil 212, the ECG sensor 214 and the ultrasound probe 144 coupled to the console 140.

The method 300 further includes detaching the drive connector 230 from the guidewire 202 (block 310). In some embodiments, detaching the drive connector 230 from the guidewire 202 occurs only after the guidewire 202 is confirmed to be in the desired anatomical location. In some embodiments, detaching the drive connector 230 from the guidewire 202 includes removing the pair of EM coil attachments 238A/B from the pair of EM coil connectors 222A/B and the ECG sensor attachment 240 from the EM sensor 224. In some embodiments, detaching the drive connector 230 from the guidewire 202 includes slidably disengaging the drive connector 230 from the proximal end of the guidewire 202. In some embodiments, slidably disengaging includes sliding the drive connector 230 proximally from the proximal end of the guidewire 202.

The method 300 further includes sliding a medical device 110 over the guidewire 202 (block 312). In some embodiments, the medical device 110 may include catheter, a peripherally inserted central catheter, a central venous catheter, a midline catheter, and an introducer.

In some embodiments, sliding the medical device 110 over the guidewire 202 occurs after detaching the driver connector 230 from the guidewire 202 has occurred. In some embodiments, the medical device 110 can include a catheter, peripherally inserted central catheter ("PICC"), central venous catheter ("CVC"), midline catheter, an introducer, a stylet or the like. In some embodiments, sliding the medical device 110 over the guidewire 202 can include confirming the medical device 110 is in the target site with one or more of the EM coil 212, the ECG sensor 214 and the ultrasound probe 144 coupled to the console 140.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device system, comprising: an elongate medical device, comprising: a proximal end including one or more sensor connectors; and a distal end including one or more sensors or emitters wired to the one or more sensor connectors, wherein the one or more sensors or emitters include one or more electromagnetic coils and one or more electrocardiogram (ECG) sensors; and a quick-release drive connector comprising a housing body including one or more sensor connector attachments including one or more electromagnetic coil attachments and one or more electrocardiogram sensor attachments, the quick-release drive connector configured to: a) slide over the proximal end of the elongate medical device and engage the one or more sensor connectors with the one or more sensor connector attachments, wherein engagement is configured to cause current to flow from the quick-release drive connector to the one or more electromagnetic coils causing generation of an electromagnetic field, and b) slide off the proximal end of the elongate medical device and disengage the one or more sensor connectors from the one or more sensor connector attachments wherein disengagement is configured to stop the current from flowing from the quick-release drive connector to the one or more sensors or emitters.

2. The medical device system according to claim 1, wherein the one or more sensor connector attachments extend from the housing body.

3. The medical device system according to claim 1, wherein the housing body includes a housing body cavity, the housing body cavity having the one or more sensor connector attachments therein.

4. The medical device system according to claim 1, wherein the quick-release drive connector is communicatively coupled to a console.

5. The medical device system according to claim 1, wherein the one or more sensors or emitters further include one or more impedance measuring devices.

6. The medical device system according to claim 1, wherein the one or more sensor connectors include one or more electromagnetic coil connectors, one or more electrocardiogram sensor connectors, or one or more impedance measuring device connectors.

7. The medical device system according to claim 1, wherein the one or more sensor connector attachments further include one or more impedance measuring device attachments.

8. The medical device system according to claim 1, wherein sliding the quick-release drive connector over the elongate medical device is configured to stabilize the elongate medical device and prevent embolization with the elongate medical device.

9. The medical device system according to claim 1, wherein the housing body includes a through-drape connection.

10. The medical device system according to claim 1, wherein the housing body is configured to be sterile disposable.

11. The medical device system according to claim 4, wherein the quick-release drive connector is wired to the console.

12. The medical device system according to claim 4, wherein the quick-release drive connector is wirelessly coupled to the console.

13. The medical device system according to claim 1, wherein the one or more sensors or emitters comprise one or more impedance measuring devices configured to perform one or more of mapping a cross-sectional area of one or more blood vessels, confirming delivery of the elongate medical device to an anatomical target location in a body, or confirming delivery of a medical device to the anatomical target location.

14. The medical device system according to claim 5, wherein the one or more sensors or emitters comprise the one or more electrocardiogram sensors, the one or more electrocardiogram sensors configured to perform one or more of confirming arrival of the elongate medical device at an anatomical target location, confirming a depth, or confirming a length.

15. The medical device system according to claim 1, wherein the elongate medical device is selected from the group consisting of a guidewire, a stylet, an introducer, and a catheter.

16. The medical device system according to claim 1, wherein the elongate medical device includes segmented depth markings.

17. A medical device insertion system, comprising: a guidewire system comprising: a guidewire comprising: a proximal end including one or more sensor connectors; and a distal end including one or more sensors or emitters wired to the one or more sensor connectors, wherein the one or more sensors or emitters include one or more electromagnetic coils and one or more electrocardiogram (ECG) sensors; and a quick-release drive connector comprising a housing body including one or more sensor connector attachments including one or more electromagnetic coil attachments and one or more electrocardiogram sensor attachments, the quick-release drive connector configured to: a) slide over the proximal end of the guidewire and engage the one or more sensor connectors with the one or more sensor connector attachments, wherein engagement is configured to cause current to flow from the quick-release drive connector to the one or more electromagnetic coils causing generation of an electromagnetic field, and b) slide off the proximal end of an elongate medical device and disengage the one or more sensor connectors from the one or more sensor connector attachments wherein disengagement is configured to stop the current from flowing from the quick-release drive connector to the one or more sensors or emitters; an ultrasound imaging system including a console, the ultrasound imaging system configured to receive information from the one or more sensors or emitters of the guidewire system, the console including one or more logic modules coupled to memory, wherein the console is communicatively coupled to a display and an ultrasound probe; and a medical device configured for insertion over the guidewire.

18. The medical device insertion system according to claim 17, wherein the one or more sensor connector attachments extend from the housing body.

19. The medical device insertion system according to claim 17, wherein the housing body includes a housing body cavity, the housing body cavity having the one or more sensor connector attachments therein.

20. The medical device insertion system according to claim 17, wherein the Quick-release drive connector is communicatively coupled to the console.

21. The medical device insertion system according to claim 17, wherein the one or more sensors or emitters further include one or more impedance measuring devices.

22. The medical device insertion system according to claim 17, wherein the one or more sensor connectors include one or more electromagnetic coil connectors, one or more electrocardiogram sensor connectors, or one or more impedance measuring device connectors.

23. The medical device insertion system according to claim 17, wherein the one or more sensor connector attachments further include one or more impedance measuring device attachments.

24. The medical device insertion system according to claim 17, wherein the housing body includes a through-drape connection and/or is sterile disposable.

25. The medical device insertion system according to claim 17, wherein the one or more logic modules may be configured to perform one or more of:
   determining an anatomical location of the guidewire;
   determining a depth or length of the guidewire;
   determining an anatomical location of the medical device threaded over the guidewire; or
   mapping one or more blood vessels.

26. The medical device insertion system according to claim 17, wherein the one or more logic modules are configured to determine the anatomical locations of the guidewire through tracking the one or more sensors or emitters.

27. The medical device insertion system according to claim 17, wherein the one or more logic modules are configured to determine anatomical locations of the medical device through tracking the one or more sensors or emitters of the guidewire as the medical device is inserted over the guidewire.

28. The medical device insertion system according to claim 25, wherein the one or more logic modules are configured to map the one or more blood vessels through tracking the one or more sensors or emitters.

29. The medical device insertion system according to claim 17, wherein the ultrasound probe includes one or more electromagnetic sensors configured to detect a magnetic field.

30. The medical device insertion system according to claim 17, wherein the medical device is selected from the group consisting of a catheter, a peripherally inserted central catheter, a central venous catheter, a midline catheter, and an introducer.

* * * * *